US009851322B2

(12) United States Patent
Dagan (10) Patent No.: US 9,851,322 B2
(45) Date of Patent: Dec. 26, 2017

(54) METHOD AND SYSTEM FOR DETECTING MALFUNCTION OF AN ELECTRIC BOILER

(71) Applicant: Itay Dagan, Givatayim (IL)

(72) Inventor: Itay Dagan, Givatayim (IL)

( * ) Notice: Subject to any disclaimer, the term of this patent is extended or adjusted under 35 U.S.C. 154(b) by 195 days.

(21) Appl. No.: 14/963,250

(22) Filed: Dec. 9, 2015

(65) Prior Publication Data

US 2016/0169960 A1 Jun. 16, 2016

(30) Foreign Application Priority Data

Dec. 10, 2014 (IL) .......................................... 236161

(51) Int. Cl.
*G01N 27/20* (2006.01)
*G01R 31/12* (2006.01)
*F24D 19/00* (2006.01)
*F24D 19/10* (2006.01)
*G01R 31/00* (2006.01)
*F24H 1/18* (2006.01)

(52) U.S. Cl.
CPC ......... *G01N 27/20* (2013.01); *F24D 19/0092* (2013.01); *F24D 19/1006* (2013.01); *F24D 2220/08* (2013.01); *F24H 1/182* (2013.01); *G01R 31/00* (2013.01)

(58) Field of Classification Search
CPC ...... G01N 27/00; G01N 27/20; G01N 27/205; G01R 31/00; G01R 31/002; G01R 31/08; F24D 19/00; F24D 19/0092; F24D 19/10; F24D 19/1006; F24D 2220/08; F24H 1/00; F24H 1/18; F24H 1/181; F24H 1/182

USPC ....... 324/500, 512, 535, 537, 551, 552, 555, 324/557
See application file for complete search history.

(56) References Cited

U.S. PATENT DOCUMENTS

| | | | | |
|---|---|---|---|---|
| 3,586,822 | A * | 6/1971 | Pastore | .................. F24H 1/225 219/486 |
| 5,353,653 | A * | 10/1994 | Watanabe | ............... F22D 1/325 165/11.1 |
| 6,129,284 | A | 10/2000 | Adams et al. | |
| 6,236,321 | B1 * | 5/2001 | Troost, IV | ............ F24H 9/0042 126/116 A |
| 6,766,835 | B1 | 7/2004 | Fima | |
| 2004/0086020 | A1 * | 5/2004 | Jordahl | .................. G01K 3/005 374/45 |
| 2010/0280665 | A1 * | 11/2010 | Fildes | ................... F24H 9/2035 700/275 |

(Continued)

*Primary Examiner* — Hoai-An D Nguyen
(74) *Attorney, Agent, or Firm* — Edward Langer ADV & Patent Attorney (57) ABSTRACT

A method for detecting malfunction of an electric boiler, the method including: a) detecting over scale accumulation by the steps of: metering the boiler's heating cycle, being a time from activating the boiler by a thermostat thereof until deactivating the boiler by the thermostat; if the heating cycle is longer than a threshold, then indicating over accumulation of scale in the boiler; b) detecting a malfunction of insulation of the boiler, by the steps of: metering the boiler's cooling cycle, being a time from deactivating the boiler by a thermostat thereof until reactivating the boiler by the thermostat; if the cooling cycle is shorter than the threshold, then indicating malfunction of insulation of the boiler; thereby allowing indicating malfunction of said boiler only by metering the heating and cooling cycles of said boiler.

17 Claims, 7 Drawing Sheets

(56) References Cited

U.S. PATENT DOCUMENTS

2011/0163759 A1*  7/2011  Ishii .................... H02H 3/162
                                              324/551
2017/0034873 A1*  2/2017  Faulkner .................. F24H 9/18
2017/0034874 A1*  2/2017  Faulkner .............. H05B 1/0202

* cited by examiner

METHOD AND SYSTEM FOR DETECTING MALFUNCTION OF AN ELECTRIC BOILER

TECHNICAL FIELD

The present invention relates to the field of boiler malfunction testing devices.

BACKGROUND ART

The term "electric boiler" refers herein to a boiler powered by electrical energy. Such a boiler comprises a water container and a heating body installed inside the container. The water container is wrapped by an insulation wrapper, and the space between the containers is filled with insulation material.

The functionality of such a boiler diminishes with time, and as a result its heating and insulation integrity decreases. The reason thereof is degradation of the circuits and of the insulating container, through use over time.

Checking the proper operation of an electric boiler usually requires the intervention of a technician who usually needs to inspect the inner side of the water container.

As such, there is a long felt need for a solution for detecting a malfunction of an electric boiler, without inspecting its inner side, and without the intervention of a technician.

It is an object of the present invention to provide a solution to the above-mentioned and other problems of the prior art.

Other objects and advantages of the invention will become apparent as the description proceeds.

SUMMARY OF THE INVENTION

The term "normalization" refers herein as to correcting a metered value to be more accurate by taking in consideration another factor.

In one aspect, the present invention is directed to a method for detecting malfunction of an electric boiler, the method comprising:
a) detecting over scale accumulation by the steps of:
metering said boiler's heating cycle, being a time from activating said boiler by a thermostat thereof until deactivating said boiler by the thermostat;
if said heating cycle is longer than said first threshold, then indicating over accumulation of scale in said boiler;
b) detecting a malfunction of an isolation of said boiler, by the steps of:
metering said boiler's cooling cycle, being a time from deactivating said boiler by a thermostat thereof until reactivating said boiler by the thermostat;
if said cooling cycle is shorter than said threshold, then indicating malfunction of an isolation of said boiler;
thereby allowing indicating malfunction of the boiler by metering only the heating and/or cooling cycles of the boiler.

The method may further comprise the steps of:
metering a surrounding temperature of the boiler;
normalizing the metered heating cycle with the temperature;
thereby obtaining an accurate indication of the malfunction of scale accumulation and conductivity of cables that provide power to the boiler.

The method may further comprise the steps of:
metering a surrounding temperature of the boiler;
normalizing the metered cooling cycle with the temperature;
thereby obtaining a more accurate indication of the insulation of the boiler.

The method may further comprise a preliminary stage comprising the steps of:
closing a circuit that includes wires connecting a heating body (16) of the boiler with an electrical power source;
providing to the circuit a voltage of between 3.3V to 12V;
metering a resistance of the circuit;
if the metered resistance is infinite, or if there is no current in the circuit, concluding there is a disconnection in the infrastructure, and/or the heating body is out of order;
if the measured resistance is greater than a resistance which is considered to be normal for the boiler, concluding that a major part of the energy for heating the boiler is wasted on conduction of the electric power rather than on heating the boiler,
thereby concluding that the effectiveness of supplied power to the boiler is decreased.

The method may further comprise the steps of: metering a power of the boiler, and correcting the heating cycle accordingly (2000 W, 2500 W, etc.).

In another aspect, the invention is directed to a system for detecting malfunction of an electric boiler, the system comprising:
a current sensor, for detecting whether current flows in a heating circuit of the boiler, being a circuit including a AC power source, thermostat and a heating body of the boiler;
a timer, for metering heating and cooling cycles of the boiler;
an analyzer adapted to detect:
(a) over scale accumulation, by comparing the heating cycle to a threshold which indicates proper operation; and
(b) malfunction of an isolation of the boiler, by comparing the cooling cycle to a cooling cycle threshold indicating proper operation.

The system may further comprise:
a relay, for switching wires that provide AC power to the boiler, to a DC power source;
a resistance sensor, for metering a resistance of the wires and boiler while being connected to the DC power source; and
an adaptation of the analyzer to determine malfunction of the wires if a metered resistance by the sensor is greater than a threshold.

According to one embodiment of the invention:
the current sensor is further adapted to meter a density of the AC current, thereby calculating a power of the boiler; and
the analyzer is further adapted to normalize the heating cycle according to the power.

According to one embodiment of the invention, the analyzer is embodied as a mechanism employing a central processor and memory for executing a code and storing data.

According to one embodiment of the invention, the analyzer is embodied as a mechanism employing an integrated circuit.

According to one embodiment of the invention, the analyzer is embodied as micro controller.

The system may further comprise:
a thermometer, for metering a surrounding temperature of the boiler; and an adaptation of the analyzer to normalize a metered cooling and/or heating cycles with the temperature; thereby obtaining a more accurate indication of the malfunction of the boiler.

The system may further comprise:
a remote center (60), adapted to carry out an operation selected from a group comprising: performing a part or all of the functionalities of the analyzer, storing in a database (62) historical malfunction tests of the boiler, alerting a user of malfunction of his boiler, obtaining from a weather server a surrounding temperature of where the boiler is installed, and so on; and
a communication interface, for communicating with the control box (40) over a network.

The communication interface may be wired, as well as wireless.

According to one embodiment of the invention, the communication interface comprises:
a Wi-Fi interface (58), for communication with the remote center (60) via a desktop computer (54), access point, router, and the like, through the Internet.

According to another embodiment of the invention, the communication interface comprises:
a cellular communication interface, for communication with the remote center (60) via a cellular network.

The reference numbers have been used to point out elements in the embodiments described and illustrated herein, in order to facilitate the understanding of the invention. They are meant to be merely illustrative, and not limiting. Also, the foregoing embodiments of the invention have been described and illustrated in conjunction with systems and methods thereof, which are meant to be merely illustrative, and not limiting.

BRIEF DESCRIPTION OF DRAWINGS

Preferred embodiments, features, aspects and advantages of the present invention are described herein in conjunction with the following drawings.

It should be understood that the drawings are not necessarily drawn to scale.

DESCRIPTION OF EMBODIMENTS

The present invention will be understood from the following detailed description of preferred embodiments ("best mode"), which are meant to be descriptive and not limiting.

For the sake of brevity, some well-known features, methods, systems, procedures, components, circuits, and so on, are not described in detail.

Figure 1:
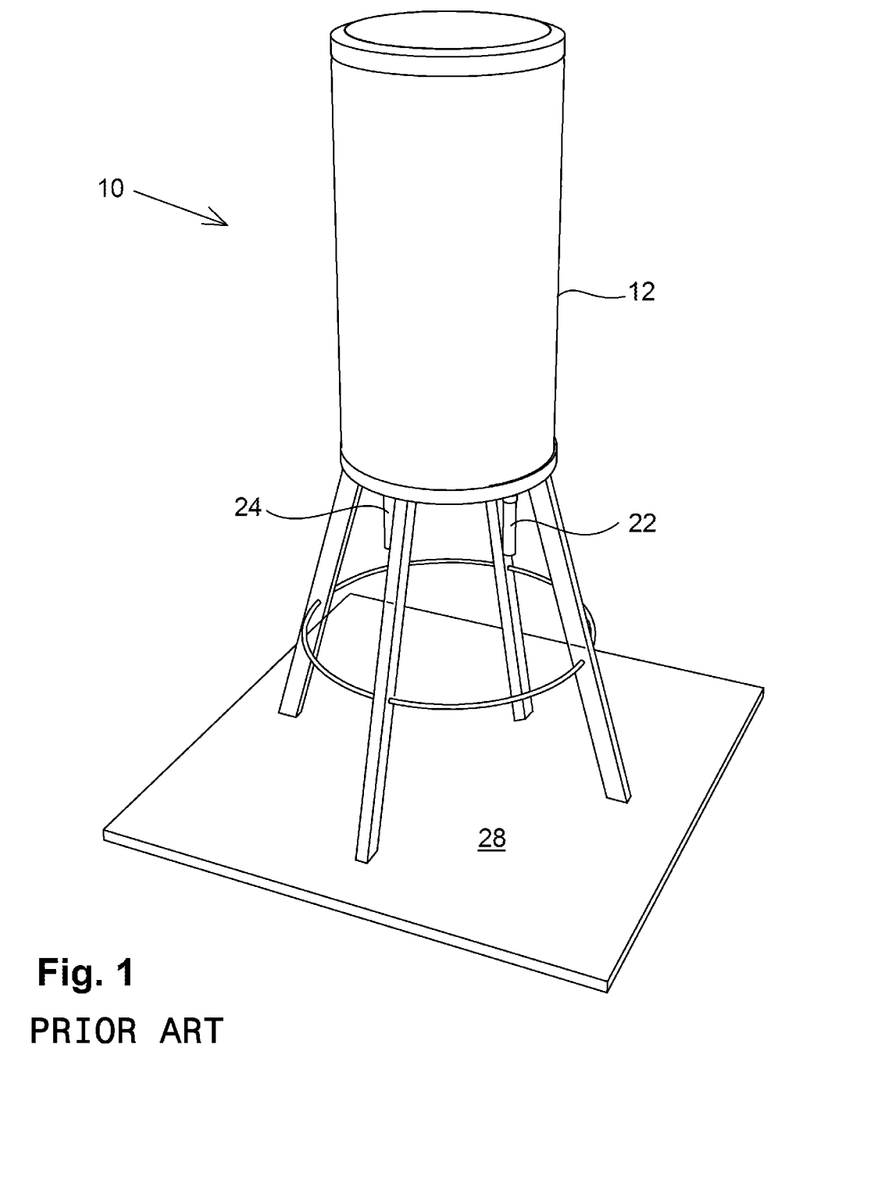
FIG. 1 is a perspective view schematically illustrating an electric boiler, according to the prior art.

FIG. 1 is a perspective view schematically illustrating an electric boiler, according to the prior art.

The electric boiler, which is marked herein by reference numeral 10, is installed on a roof 28. However, it should be noted that electric boilers may also be installed indoors.

Two pipes are connected to the boiler. The water enters into the water container of the boiler through pipe 22, and the heated water exits the water container through pipe 24.

Figure 2:
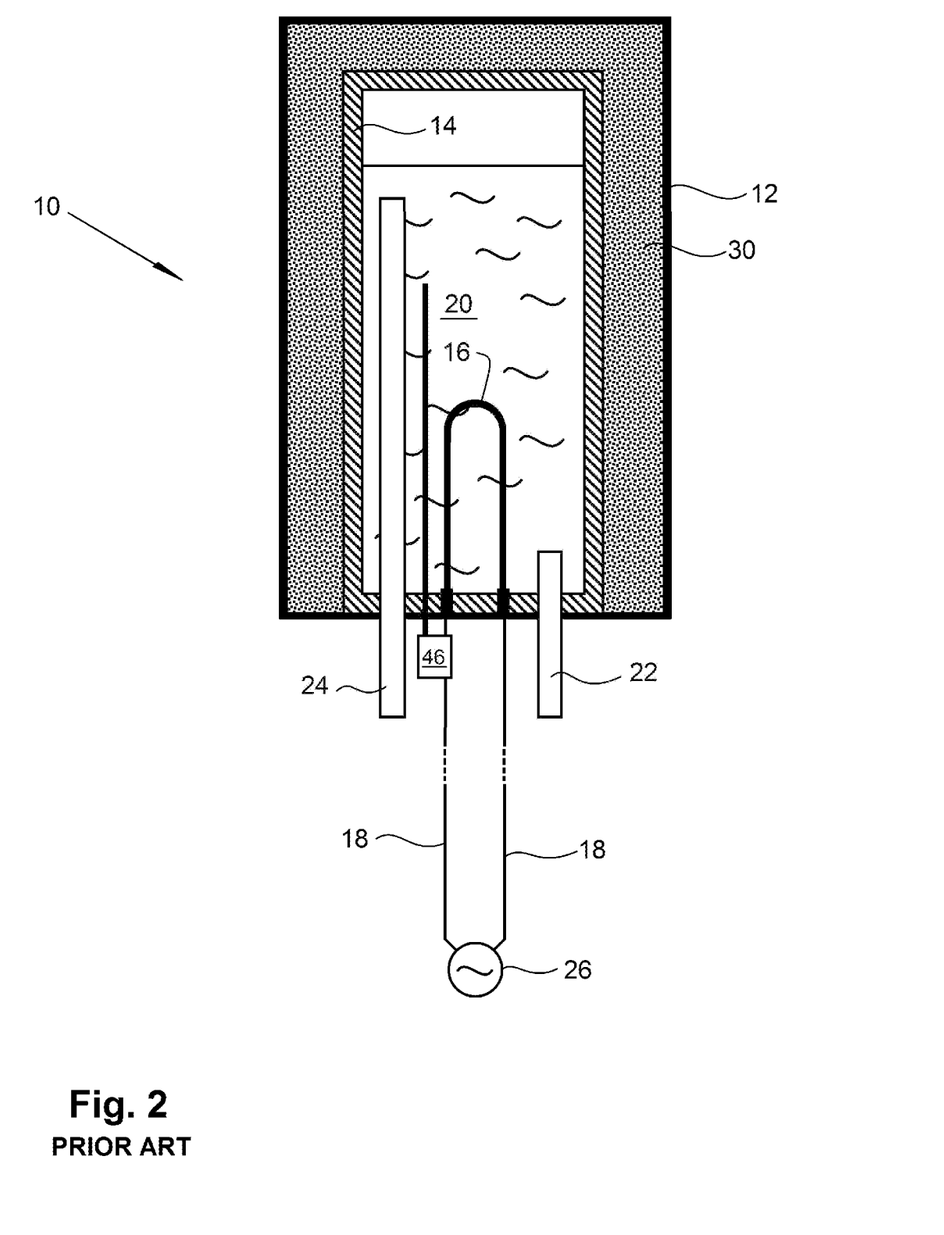
FIG. 2 is a sectional view schematically illustrating an electric boiler, according to the prior art.

FIG. 2 is a sectional view schematically illustrating an electric boiler, according to the prior art.

The boiler 10 heats the water 20 of the water container 14 by a heating body 16 by providing power through the AC power source 26.

Wires 18 that connect the heating body 16 with the power source 26 are also referred to herein as "infrastructure".

The boiler is placed into an insulation wrapper 12. An insulation material 30 is disposed between the water container 14 and the insulation wrapper 12.

Figure 3:
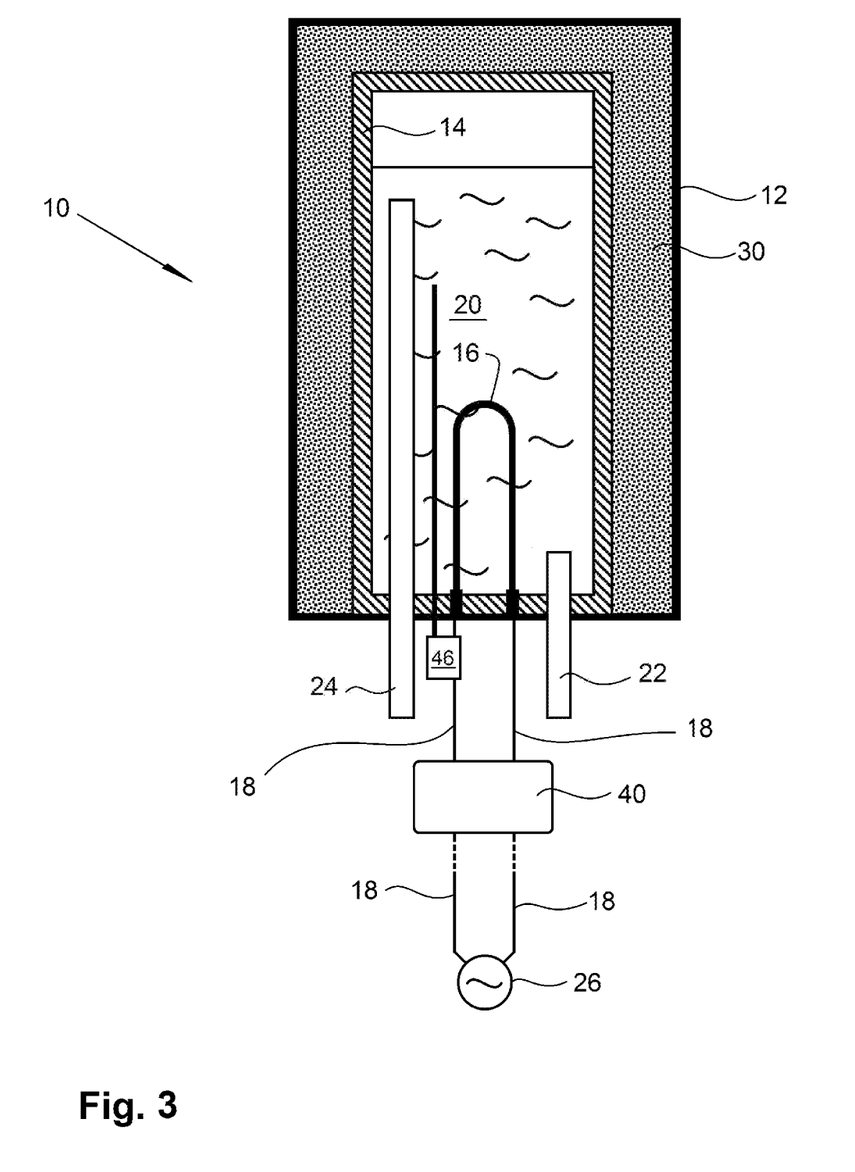
FIG. 3 is a sectional view schematically illustrating an electric boiler in which is installed a system for detecting malfunction thereof, according to one embodiment of the invention.

FIG. 3 is a sectional view schematically illustrating an electric boiler in which is installed a system for detecting malfunction thereof, according to one embodiment of the invention.

The system is embodied as a control box 40 which is connected to wires 18 through which AC power is provided from the domestic AC power source 26.

From the power supply point of view, the electric boiler has three states: on, off and circuit check. In the on state, AC power is supplied to the boiler, i.e., the circuit that provides power to the boiler is closed. In the off state this circuit is disconnected, and therefore no electric power is supplied to the boiler. In the circuit check state, a low voltage DC (converted form AC power) is running through the circuit.

In testing malfunction of a boiler, the following steps are carried out:

Step 1: Checking if there is a disconnection or waste of energy in the electric circuit of the boiler is carried out by using a low voltage DC circuit which is supplied by the control box and includes the infrastructure (i.e., the wires 18 that connect the electrical power source 26) and heating body.

In this situation the circuit that comprises the infrastructure and the heating body is connected to a low voltage DC power supply (such as between 3.3V to 12V), and the resistance of the circuit is measured.

If the resistance is infinite (i.e., there is no current in the circuit), it means that there is a disconnection in the infrastructure, and/or the heating body is out of order. This test is carried out assuming the thermostat is working properly If the measured resistance is greater than the expected resistance which is considered to be normal, it means that a major part of the energy for heating the boiler is wasted on conduction of the electric power rather than on heating the boiler, and as a result, the effectiveness of the boiler is decreased.

If the results of this test show proper operation of the boiler, then the rest of the tests take place.

Step 2: Measuring the heating and cooling cycles of the boiler is carried out as follows:

The thermostat is a component connected in serial circuit to a heating body and in charge of normalizing the water's temperature using feedback to cut/connect the circuit according to two temperature thresholds. When the water temperature gets less than a low threshold (marked herein as "L"), the circuit is closed and the heating body is activated.

In this situation, when the water temperature gets higher than a threshold (marked herein as "H"), the circuit is opened and the heating body is deactivated. The time difference between L and H is referred to herein as a heating cycle.

When the water temperature gets higher than the high threshold (marked herein as "H"), the circuit opens and the heating body is deactivated. When the water temperature gets less than a low threshold (marked herein as "L"), the circuit closes and the heating body is reactivated. The time difference between H and L is referred to herein as to a cooling cycle.

Thus, according to the present invention, the heating and cooling cycles are used as indicators to the heating and cooling rate.

In case the heating cycle is infinite or at least above a reasonable time required to heat the water (considering the specific boiler's properties), an alert can be sent to inform the user about a malfunction of the boiler.

Step 3: Checking the physical deterioration of the boiler's insulation is carried out as follows:

If the boiler's insulation shows physical deterioration, then the cooling cycle is less in comparison to the expected normal rate. The greater the cooling cycle, the better the insulation of the boiler's container. It is like a cooling pot: if the pot is covered, the cover provides some insulation, and therefore the cooling cycle will be greater (i.e., slower) than if the pot is not covered.

Assuming the normal cooling cycle is measured in a new installed boiler, the result of this measurement can be taken in consideration as the normal cooling cycle of the boiler.

Step 4: Measuring the scale accumulation is carried out as follows:

The scale acts like an insulation of the heating body from the water that surrounds it, and therefore accumulation of scale prolongs the heating cycle of the boiler. As a result, the electricity consumption of the boiler increases.

A "new" boiler contains no scale, and therefore the heating cycle of a new boiler can be taken as an indicator for ideal operation. The longer the heating cycle in comparison to the ideal heating cycle, the larger the accumulated scale.

Additionally or alternatively, the heating cycle can be compared to the heating cycle of other boilers of the same characteristics, brand, and so on. Thus, the normal heating cycle does not necessarily have to be measured on a recently installed boiler, but rather can be provided to the component that carries out the comparison (as detailed later).

Preferably, a certain heating cycle can be defined as an alert, and a higher heating cycle can be defined as a failure.

The conductivity of the infrastructure (i.e., wires 18 through which electric power is provided to the heating body of the boiler) also have impact on the heating cycle, especially in a boiler installed on a roof, as these cables are "long" in comparison to an indoor installed boiler. An inappropriate or a worn out cable can also affect the infrastructure conductivity. Thus, the normal infrastructure conductivity can be measured when the boiler is "new", i.e., recently installed. This test can also be carried out during the test of step 1.

Taking into consideration the surrounding temperature, a more accurate result about the malfunction of the boiler can be obtained. For example, the impact of the surrounding on the heating and cooling cycle can be inquired, and introduced into a formula that corrects the results of the tests, taken into consideration and used as an input data to calculate the tests results.

This can be carried out for a particular brand of boilers, a boiler of specific water capacity, a boiler in general, as well as for an individual boiler.

Figure 4:
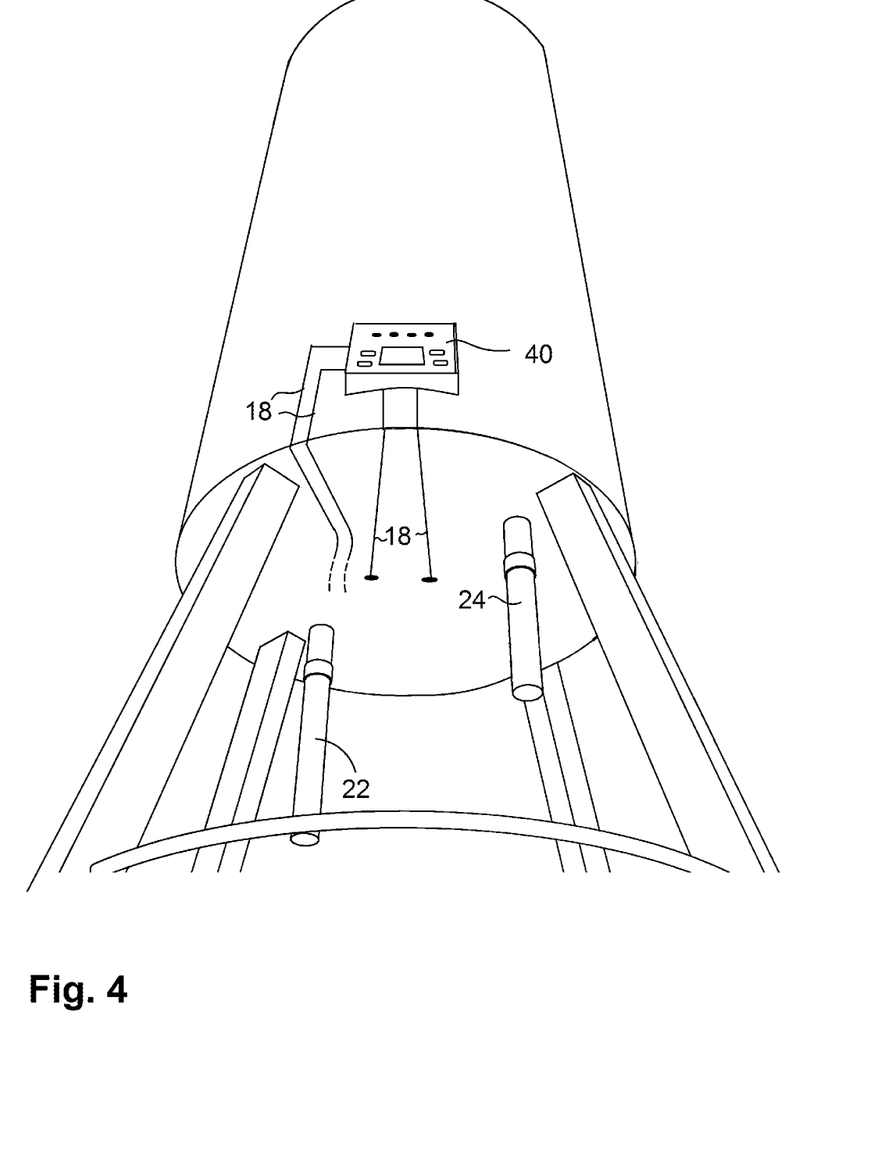
FIG. 4 pictorially illustrates an electric boiler in which is installed a system for detecting malfunction thereof, according to a basic embodiment of the invention.

FIG. 4 pictorially illustrates an electric boiler in which is installed a system for detecting malfunction thereof, according to a basic embodiment of the invention.

Figure 5:
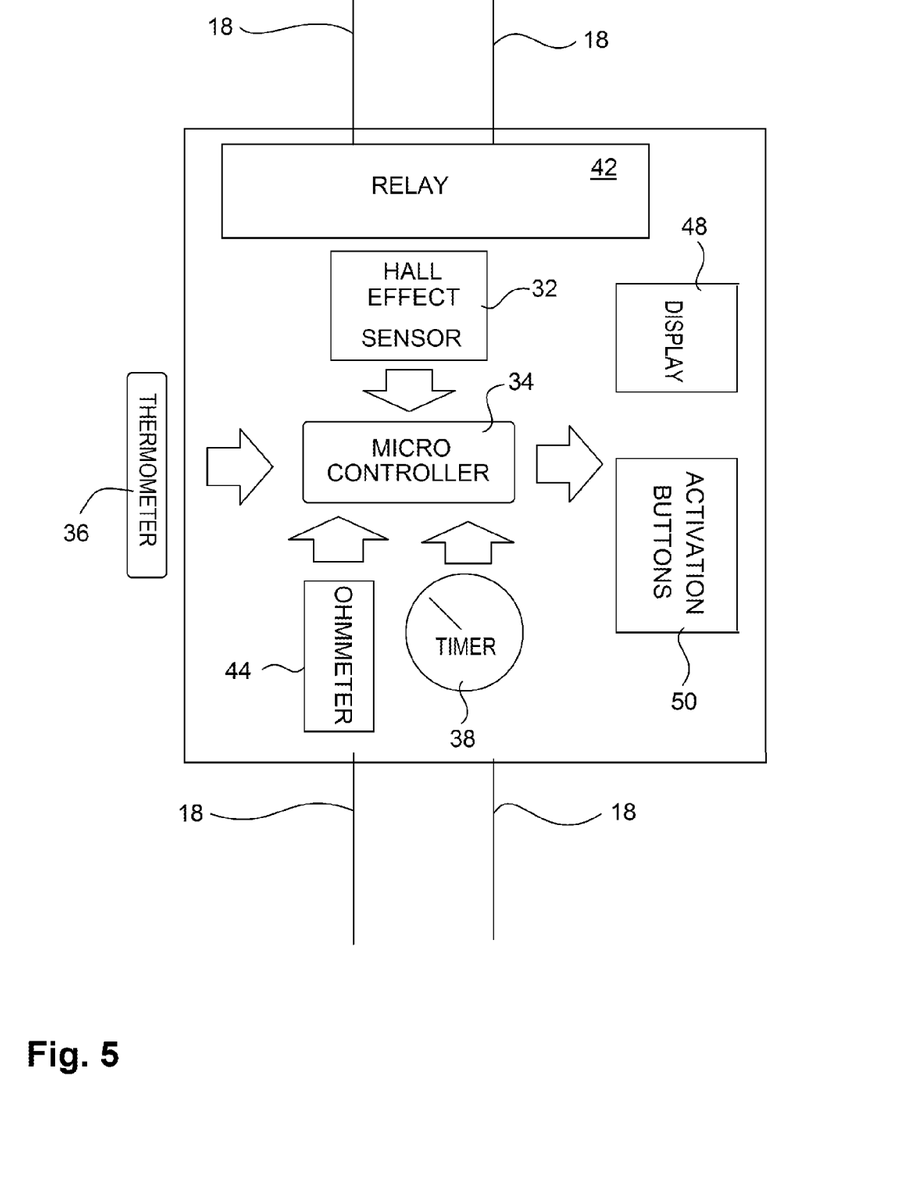
FIG. 5 is a block diagram that schematically illustrates the system of FIG. 4.

FIG. 5 is a block diagram that schematically illustrates the system of FIG. 4.

The system is placed in a control box 40. The control box comprises a user interface which may include activation buttons 50 for manually initiating a test, LEDs or LCD 48 for providing indication on the test results, and so on. The user may use the user interface to provide to the processor of the control box parameters of the boiler, such as its volume, power (e.g., 2000 W or 2500 W), and so on.

An ohmmeter 44 meters the resistance of wires 18 which connects the boiler with an electric power source.

The value measured by the ohmmeter is provided to an analyzer, which may be implemented as a code executed by a micro controller, a computerized mechanism (i.e., a mechanism that comprises memory for storing the code and data, and central processor for executing the code), integrated circuit, and so on.

The analyzer conducts a test according to the steps described above. The results of the test are displayed on the display 48, indication LEDs, and so on.

Optionally, the system may comprise a thermometer 36 for testing the surrounding temperature of the boiler. This result is provided to the analyzer, which normalizes the measurement for providing a more accurate result, thereby obtaining a more accurate conclusion about malfunction of the boiler.

The Hall Effect sensor may also measure the current density. This information is useful for determining the power of the boiler (e.g., 2000 W, 2500 W, etc.) and correcting the value of the heating cycle accordingly. The power of the boiler can also be determined from the resistance and the AC voltage.

Figure 6:
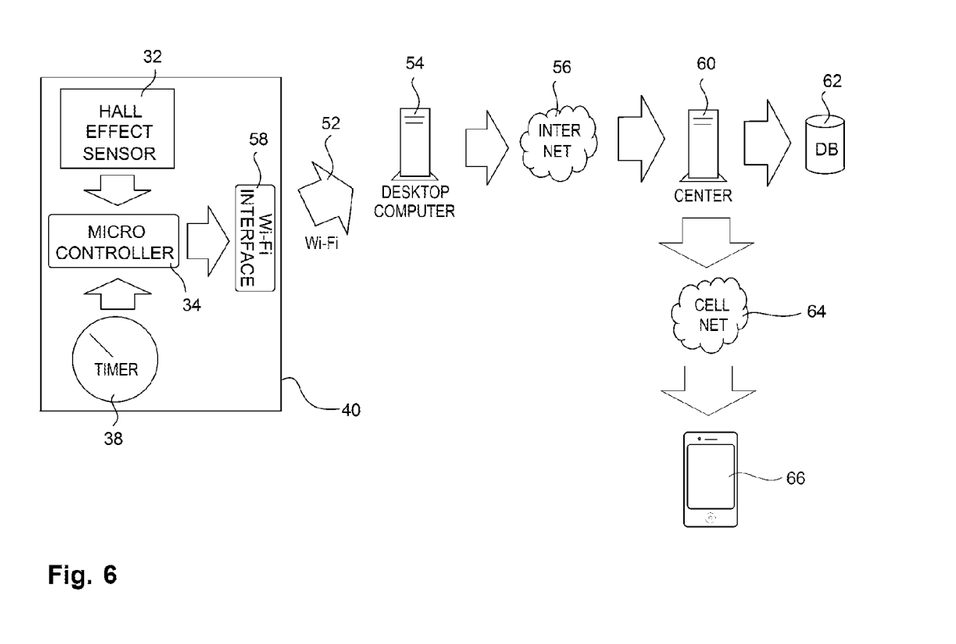
FIG. 6 is a block diagram schematically illustrating a system for detecting malfunction of an electric boiler, according to an advanced embodiment of the invention.

FIG. 6 is a block diagram schematically illustrating a system for detecting malfunction of an electric boiler, according to an advanced embodiment of the invention.

The difference between the embodiment of FIG. 5 and the embodiment of FIG. 6 is that while in the embodiment of FIG. 5 all the components of the system are embedded in control box 40, in the embodiment of FIG. 6 the system cooperates with a remote center 60 which may replace operations of micro controller 34, and even the thermometer (as the surrounding temperature may be obtained from an online weather service), and so on.

The remote center 60, which may be implemented as one or more servers, may replace the analyzer of the embodiment of FIG. 5. In other words, the remote center 60 obtains the results of the tests carried out by the analyzer, stores the information in the database 62, uses this information for detecting malfunction of a certain brand of boilers, obtains the current surrounding temperature of the boiler from a weather service or from a thermometer installed at the boiler, normalizes the result, and so on.

In order to communicate with the remote center 60, in control box 40 is installed, for example, a Wi-Fi communication interface 58. The Wi-Fi interface 58 communicates through Wi-Fi communication 52 with a domestic desktop computer 54, which communicates with the remote center 60 via the Internet 56.

Actually, a better solution is using a domestic access point such as a router.

Actually, the Wi-Fi communication interface is merely an example, and other forms of wireless communication interface may be used. Furthermore, a wired communication may also be employed for this purpose.

According to one embodiment of the invention, the step of communicating with a domestic access point is skipped, and the control box may communicate with remote center 60 by cellular communication.

It should be noted that the analyzer may reside in control box 40, as well as in the remote center 60.

The remote center 60 may send instructions to display the result to the desktop computer in the same way. The remote center may also send the result to the user's cellular telephone 66 through cellular network 64, to alert the user through his cellular telephone, and so on.

On the cellular telephone side an agent may be operated in a form of an application program. The application program may also be used as an analyzer, as a test initiating component, and so on. Thus, the malfunction tests may be launched by a user, as well as by the remote center, or the application program.

According to another embodiment of the invention, instead of the Wi-Fi that communicates with the remote server through the Internet, control box 40 may comprise a cellular interface that communicates with the remote server through a cellular network.

Figure 7:
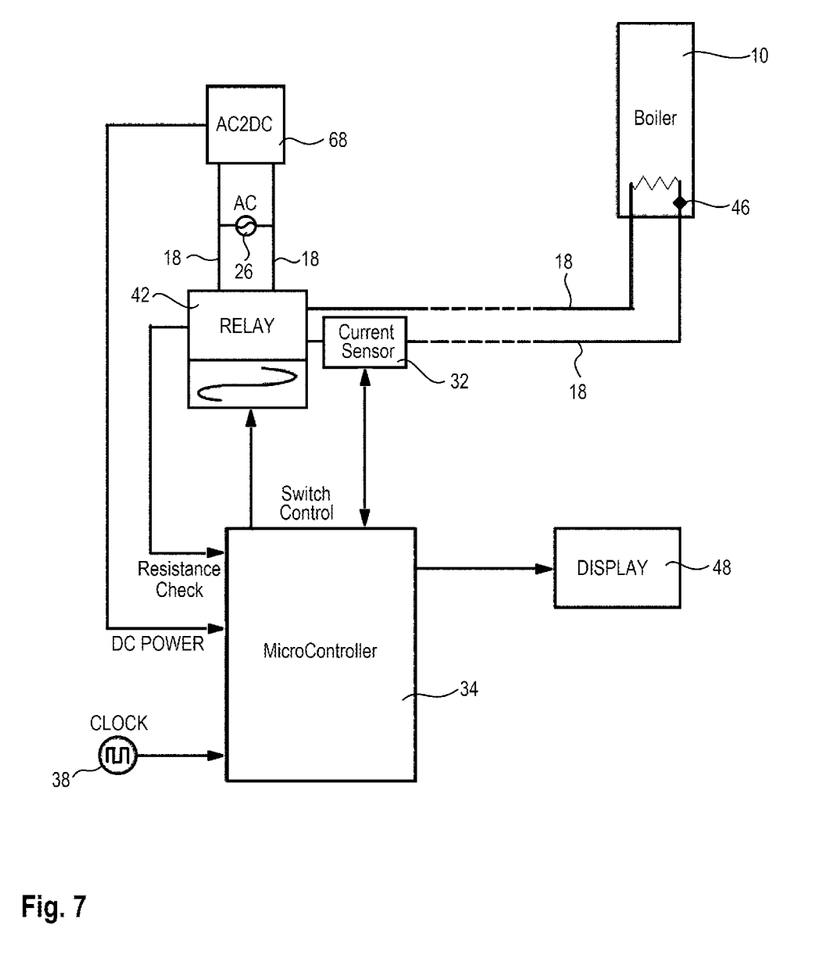
FIG. 7 schematically illustrates an integrated circuit of a system for detecting malfunction thereof, according to one embodiment of the invention.

FIG. 7 schematically illustrates an integrated circuit of a system for detecting malfunction thereof, according to one embodiment of the invention.

Micro controller 34 operates as an analyzer to which sensor measurements are provided. Such measurements are the input of a clock (timer), the reading of a current sensor 32 (such as a Hall Effect sensor) which detects presence of current in the infrastructure wires 18 and measures the current density thereof.

The circuit includes an AC2DC (i.e., AC to DC) converter 68, which converts the AC power to DC power according to instructions from the Micro Controller 34.

In the first step (Step 1) mentioned above, the Micro controller 34 switches the relay to the low DC voltage (3.3V to 12V). In this situation, the Micro controller measures the resistance of the infrastructure and the heating body.

In the next step (Step 2), the Micro controller switches to the AC voltage, and the boiler is activated. While the boiler heats, the current is monitored by the current sensor 32 until the thermostat 46 cuts the power supply circuit. The time taken from threshold "L" (low temperature limit) to threshold "H" (high temperature limit) is defined as the heating cycle.

At this stage the boiler cools, until its water temperature gets below a thermostat threshold. At this stage the thermostat closes the heating circuit. This event is detected by the Micro controller, which considers it as the cooling cycle.

The micro controller compares the heating and cooling cycles to thresholds which are considered to indicate normal operation of the boiler, and if the measured heating and cooling cycles are beyond these thresholds, the micro controller alerts the user thereabout.

The greater the difference between a measured cycle and the threshold thereof, the less efficient the indicated feature. For example, the greater the heating cycle, the more scale is accumulated; the greater the cooling cycle, the less efficient is the boiler's insulation. Of course, the measured values can be shown on a scale, such as good, reasonable, poor.

In the figures and/or description herein, the following reference numerals (Reference Signs List) have been mentioned:

numeral 10 denotes an electric boiler;
numeral 12 denotes an insulation wrapper;
numeral 14 denotes a water container;
numeral 16 denotes a heating body;
numeral 18 denotes wires that connect the heating body 16 with the power source 26;
numeral 20 denotes water;
numeral 22 denotes a pipe through which water enters into the water container 14;
numeral 24 denotes a pipe through which hot water exits from the water container 14;
numeral 26 denotes an electric power source;
numeral 28 denotes a roof;
numeral 30 denotes an insulation material;
numeral 32 denotes a Hall Effect sensor;
numeral 34 denotes an analyzer, which in some embodiments of the present invention is applied by a micro controller;
numeral 36 denotes a temperature sensor, which according to some embodiments of the invention is applied by a thermometer;
numeral 38 denotes a timer/clock;
numeral 40 denotes a control box;
numeral 42 denotes a relay;
numeral 44 denotes a resistance sensor, which in some embodiments of the invention is applied by an ohmmeter;
numeral 46 denotes a thermostat of the boiler;
numeral 48 denotes a display;
numeral 50 denotes activation buttons;
numeral 52 denotes a Wi-Fi communication;
numeral 54 denotes a domestic desktop computer, access point (router), and so on;
numeral 56 denotes the Internet;
numeral 58 denotes a Wi-Fi interface;
numeral 60 denotes a remote center, which according to some embodiments of the invention is applied by one or more servers;
numeral 62 denotes a database;
numeral 64 denotes a cellular network;
numeral 66 denotes a cellular telephone/Smartphone; and
numeral 68 denotes an AC to DC converter.

The foregoing description and illustrations of the embodiments of the invention have been presented for the purposes of illustration. It is not intended to be exhaustive or to limit the invention to the above description in any form.

Any term that has been defined above and used in the claims, should to be interpreted according to this definition.

The reference numbers in the claims are not a part of the claims, but rather used for facilitating the reading thereof. These reference numbers should not be interpreted as limiting the claims in any form.

The invention claimed is:

1. A method for detecting malfunction of an electric boiler, the method comprising:
   a) detecting over scale accumulation by the steps of:
   metering said boiler's heating cycle, being a time from activating said boiler by a thermostat thereof until deactivating said boiler by the thermostat;
   if said heating cycle is longer than a threshold, then indicating over accumulation of scale in said boiler;
   b) detecting a malfunction of insulation of said boiler, by the steps of:
   metering said boiler's cooling cycle, being a time from deactivating said boiler by a thermostat thereof until reactivating said boiler by the thermostat;

if said cooling cycle is shorter than said threshold, then indicating malfunction of insulation of said boiler;

thereby allowing indicating malfunction of said boiler only by metering the heating and cooling cycles of said boiler.

2. A method according to claim 1, further comprising the steps of:
   metering a temperature of a surrounding of said boiler;
   normalizing the metered heating cycle with said temperature;
thereby obtaining an accurate indication of the malfunction of scale accumulation and conductivity of cables that provide power to said boiler.

3. A method according to claim 1, further comprising the steps of:
   metering a surrounding temperature of said boiler;
   normalizing the metered cooling cycle with said temperature;
thereby obtaining a more accurate indication of the insulation of said boiler.

4. A method according to claim 1, further comprising a preliminary stage comprising the steps of:
   closing a circuit that includes wires connecting a heating body (16) of said boiler with an electrical power source;
   providing to said circuit a voltage of between 3.3V to 12V;
   metering a resistance of said circuit;
   if the metered resistance is infinite, or if there is no current in said circuit, concluding there is a disconnection in the infrastructure, and/or the heating body is out of order;
   if the measured resistance is greater than a resistance threshold which is considered to be normal for said boiler, concluding that a major part of the energy for heating said boiler is wasted on conduction of the electric power rather than on heating said boiler,
thereby concluding that the effectiveness of supplied power to said boiler is decreased.

5. A method according to claim 1, further comprising the step of: metering a power of said boiler, and correcting said heating cycle accordingly.

6. A system for detecting malfunction of an electric boiler, the system comprising:
   a current sensor, for detecting whether current flows in a heating circuit of said boiler, being a circuit including an AC power source, thermostat and a heating body of said boiler;
   a timer, for metering heating and cooling cycles of said boiler;
   an analyzer adapted to detect:
      (a) over scale accumulation, by comparing said heating cycle to a threshold which indicates proper operation; and
      (b) malfunction of insulation of said boiler, by comparing said cooling cycle to a cooling cycle threshold indicating proper operation.

7. A system according to claim 6, further comprising:
   a relay, for switching wires that provide AC power to said boiler, to a DC power source;
   a resistance sensor, for metering a resistance of said wires and boiler while being connected to said DC power source; and
   an adaptation of said analyzer to determine malfunction of said wires if a metered resistance by said sensor is greater than a threshold resistance.

8. A system according to claim 6, wherein:
   said current sensor is further adapted to meter intensity of said AC current flow, thereby calculating a power of said boiler; and
   said analyzer is further adapted to normalize said heating cycle according to said power.

9. A system according to claim 6, wherein said analyzer is embodied as a mechanism employing a central processor and memory for executing a code and storing data.

10. A system according to claim 6, wherein said analyzer is embodied as a mechanism employing an integrated circuit.

11. A system according to claim 6, wherein said analyzer is embodied as a micro controller.

12. A system according to claim 6, further comprising:
   a thermometer, for metering a surrounding temperature of said boiler; and
   an adaptation of said analyzer to normalize a metered cooling and/or heating cycle with said temperature;
thereby obtaining a more accurate indication of the malfunction of said boiler.

13. A system according to claim 6, further comprising:
   a remote center (60), adapted to carry out an operation selected from a group comprising: performing a part or all of the functionalities of said analyzer, storing in a database (62) historical malfunction tests of said boiler, alerting a user of malfunction of his boiler, obtaining from a weather server a surrounding temperature of where said boiler is installed, and so on; and
   a communication interface, for communicating with said control box (40) over a network.

14. A system according to claim 13, wherein said communication interface is wired.

15. A system according to claim 13, wherein said communication interface is wireless.

16. A system according to claim 13, wherein said communication interface comprises:
   a Wi-Fi interface (58), for communication with said remote center (60) via a desktop computer (54), access point, router, and the like, through the Internet.

17. A system according to claim 13, wherein said communication interface comprises:
   a cellular communication interface, for communication with said remote center (60) via a cellular network.

* * * * *